US008514068B2

(12) United States Patent  (10) Patent No.: US 8,514,068 B2
Katingari et al.  (45) Date of Patent: *Aug. 20, 2013

(54) PULSE WIDTH CODING FOR INTERFERENCE-TOLERANT TELEMETRIC SIGNAL DETECTION

(75) Inventors: Karthik H. Katingari, Milpitas, CA (US); Thomas Ying-Ching Lo, Fremont, CA (US)

(73) Assignee: Salutron, Inc., Fremont, CA (US)

( * ) Notice: Subject to any disclaimer, the term of this patent is extended or adjusted under 35 U.S.C. 154(b) by 842 days.

This patent is subject to a terminal disclaimer.

(21) Appl. No.: 12/711,114

(22) Filed: Feb. 23, 2010

(65) Prior Publication Data

US 2011/0205051 A1   Aug. 25, 2011

(51) Int. Cl.
  *G08B 1/08*   (2006.01)
(52) U.S. Cl.
  USPC ....................................... 340/539.12
(58) Field of Classification Search
  USPC ............... 340/539.12, 573.1, 870.24, 13.24, 340/539.1; 600/519, 520, 523
  See application file for complete search history.

(56) References Cited

U.S. PATENT DOCUMENTS

| | | | |
|---|---|---|---|
| 5,611,346 A | | 3/1997 | Heikkila et al. |
| 5,632,279 A | | 5/1997 | Heikkila |
| 5,738,104 A | | 4/1998 | Lo et al. |
| 5,743,269 A | * | 4/1998 | Okigami et al. ............ 600/509 |
| 5,876,350 A | * | 3/1999 | Lo et al. ..................... 600/519 |
| 6,332,094 B1 | * | 12/2001 | Gorman ...................... 600/520 |
| 6,449,509 B1 | | 9/2002 | Park et al. |
| 6,473,008 B2 | | 10/2002 | Kelly et al. |
| 6,496,546 B1 | | 12/2002 | Allpress et al. |
| 6,961,374 B2 | | 11/2005 | Chen |
| 7,030,735 B2 | * | 4/2006 | Chen ........................... 340/323 R |
| 7,129,835 B2 | | 10/2006 | Nikkola |
| 2002/0038094 A1 | * | 3/2002 | Gorman ...................... 600/520 |

(Continued)

FOREIGN PATENT DOCUMENTS

| | | |
|---|---|---|
| JP | 62091876 A | 4/1987 |
| WO | 9641290 | 12/1996 |

OTHER PUBLICATIONS

Non-final Office Action dated Nov. 5, 2012, U.S. Appl. No. 12/819,892 filed Jun. 21, 2010.

(Continued)

*Primary Examiner* — Phung Nguyen
(74) *Attorney, Agent, or Firm* — Vierra Magen Marcus LLP (57) ABSTRACT

A monitor provides a wireless signal with respective pulses, based on a heartbeat, repetitive physical movement, or other repetitive bodily action of a user. The pulses include longer duration pulses whose duration identifies the monitor, and distinguishes it from other monitors which may provide crosstalk interference. The longer duration pulses are interspersed among short duration pulses to reduce power consumption. A receiver unit processes the signal to determine a rate of the bodily action and provide a corresponding output. The receiver unit can operate in a baseline mode when crosstalk is not detected, where each pulse is used to determine the rate, or in a crosstalk mode when crosstalk is detected, where only the longer duration pulses are used to determine the rate. The receiver unit can synchronize with two or more consecutive longer duration pulses. The pulse duration can be fixed or determined dynamically, e.g., non-deterministically.

31 Claims, 6 Drawing Sheets

(56) References Cited

U.S. PATENT DOCUMENTS

| | | |
|---|---|---|
| 2005/0135039 A1 | 6/2005 | Klemetti |
| 2006/0247549 A1 | 11/2006 | Chan |
| 2007/0176819 A1 | 8/2007 | May |
| 2009/0043217 A1 | 2/2009 | Hui et al. |
| 2010/0070669 A1 | 3/2010 | Johnson et al. |
| 2010/0097259 A1 | 4/2010 | Zhang |
| 2010/0331714 A1* | 12/2010 | Hui et al. ............... 600/519 |

OTHER PUBLICATIONS

Cha-Co International Company Limited, Wireless Digital Heart Rate Belt, CH9005 KIT, p. 1-9, Jun. 23, 2009.
U.S. Appl. No. 12/711,114, filed Feb. 23, 2010.
Response to Office Action dated Feb. 4, 2013, U.S. Appl. No. 12/819,892, filed Jun. 21, 2010.
Notice of Allowance and Fee(s) Due dated Mar. 4, 2013, U.S. Appl. No. 12/819,892, filed Jun. 21, 2010.

* cited by examiner

PULSE WIDTH CODING FOR INTERFERENCE-TOLERANT TELEMETRIC SIGNAL DETECTION

BACKGROUND

Wireless monitors are commonly used during exercise, athletic competitions, medical tests and other activities. For example, a heart rate monitor can be worn by a user, contacting the user at a suitable location such as the chest or wrist. A chest-worn monitor may detect an electrocardiogram (EKG) signal of the user's heart, each time a heart beat occurs, and transmit a corresponding pulse in a wireless signal to a receiver unit, where the signal is further processed to determine the heart rate. The receiver unit typically includes a display device which displays the heart rate to the user or other person. For example, the receiver unit can be worn on the user's wrist, provided in a console or other unit which is mounted to an exercise device such as a treadmill or bicycle, or provided in a portable or stationary device which is monitored by an athletic trainer, medical personnel or others.

In addition to monitoring of a heart rate, monitors are available for monitoring other bodily actions, such as breathing, or repetitive physical movements which are performed by a user during exercise, such as steps taken while running, or pedal revolutions during bicycling, and so forth. However, when wireless monitors are used in the same location, crosstalk can occur, preventing the receiver unit from accurately determining a rate at which the bodily action is performed. Other noise sources can also prevent the receiver unit from distinguishing the signal from a monitor. To this end, techniques have been developed for encoding additional identifying data onto the wireless signal. However, the existing approaches have drawbacks such as increased cost, power consumption, and complexity and susceptibility to additional sources of electromagnetic interference.

SUMMARY

A user-worn monitor, receiver unit and associated methods are provided for interference-tolerant telemetric signal detection.

In one embodiment, a receiver unit includes a receiver circuit, an amplifier circuit, a microprocessor associated with the amplifier circuit and an output device associated with the microprocessor. The receiver circuit receives a wireless signal from a user-worn monitor, where the wireless signal includes respective pulses generated by the user-worn monitor. Each respective pulse is generated when a respective instance of a bodily action of the user is detected, and the respective pulses include identifier pulses which each have a duration or width which identifies the user-worn monitor, interspersed among other pulses. The amplifier circuit provides an amplified signal based on the wireless signal. The microprocessor operates in a crosstalk tolerant mode in which it processes the amplified signal to interpret the duration of each of the identifier pulses as an identifier of the user-worn monitor. In this mode, the microprocessor also synchronizes with the identifier pulses, and determines a rate of the bodily action based on (a) time intervals between the identifier pulses and (b) a number of pulses between the each of the identifier pulses. The output device provides an output such as a display and/or audio output, based on the rate.

In another embodiment, a receiver unit includes a receiver circuit, an amplifier circuit associated with the receiver circuit, a microprocessor associated with the amplifier circuit, and a display device associated with the microprocessor. The receiver circuit receives a wireless signal from a user-worn monitor, where the wireless signal includes respective pulses generated by the user-worn monitor. Each respective pulse is generated when a respective instance of a bodily action of the user is detected, and the respective pulses include: (a) at least two consecutive identifier pulses which each have a duration which identifies the user-worn monitor, and (b) other pulses. The amplifier circuit provides an amplified signal based on the wireless signal. The microprocessor processes the amplified signal to interpret the duration of each of the at least two consecutive identifier pulses as an identifier of the user-worn monitor, determines a time interval between each of the at least two consecutive identifier pulses, synchronizes with the other pulses based on the time interval, and determines a rate of the bodily action based on timing of the other pulses (as well as timing of the at least two consecutive identifier pulses). The output device provides an output based on the rate.

In another embodiment, a user-worn monitor includes an amplifier circuit, a microcontroller associated with the amplifier circuit, and a transmitter associated with the microcontroller and the amplifier circuit. The amplifier circuit receives a signal regarding a bodily action of a user and provides a corresponding amplified signal. The transmitter provides a wireless signal based on the amplified signal, where the wireless signal includes respective pulses. Each respective pulse is generated when a respective instance of the bodily action is detected, and the respective pulses include identifier pulses which each have a duration which is set in response to the microcontroller to identify the user-worn monitor, interspersed among other pulses.

Corresponding methods may also be provided, along with a tangible processor-readable medium which stores code which is executable by a microprocessor to perform the methods described herein.

DETAILED DESCRIPTION

Difficulties which are encountered by the presence of crosstalk and other forms of interference in a wireless signal are overcome to enable accurate communication between a user-worn monitor and an associated receiver unit. At the same time, advantages are achieved with regard to cost, power consumption, complexity and susceptibility to electromagnetic interference.

Figure 1:
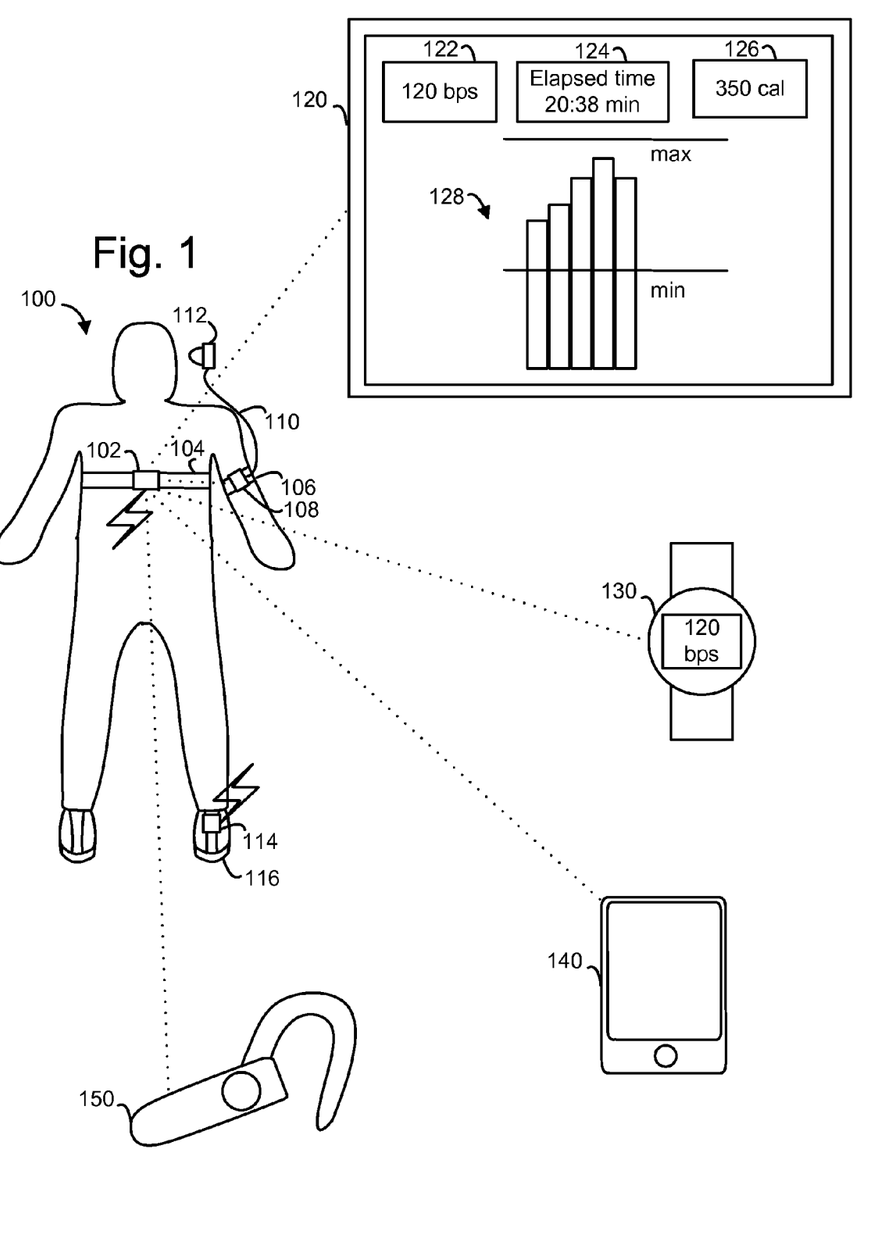
FIG. 1 depicts an example environment in which a monitor and a receiver unit are used.

FIG. 1 depicts an example environment in which a monitor and a receiver unit are used. Monitors can be used in a variety of environments. A typical application involves a user who is exercising for fitness or medical testing. Generally, a monitor can detect repetitive bodily actions. These include physiological actions such as a heart beating and breathing. A beating heart generates a low level of electrical activity in an EKG signal which can be detected by electrodes of a monitor, when the electrodes are held in contact with the user's skin. For example, the monitor 102 can be secured to an elastic strap 104 so that electrodes on the back side of the module are held against, e.g., the user's chest, back, or other portion of the torso. A heart beat can be detected by other approaches as well. For example, a monitor may use transmit ultrasonic signals into the user's body in a location of an artery, such as the radial artery in the wrist, and detect the reflected signal. Variations in the reflected signal due to blood flow in the artery can be correlated with a heart rate. Similarly, a breathing or respiration rate can be detected by a chest strap which continuously measures an extent to which it expands and contracts. Or, typically in a medical environment, a motion sensor can measure movement of the chest to determine respiration rate.

It is also useful to measure repetitive bodily actions such as repetitive physical movements which are performed by a user during exercise, such as steps taken while walking or running, pedal revolutions during bicycling, and so forth. Other examples include jump rope skips, and bodily action related to calisthenics such as lunges, jumping jacks, sit-ups, stomach crunches, push-ups, pull-ups, squats, calf-raises, toe touches, and dips. Other examples of repetitive bodily actions include muscle movements performed during weight training, such as leg or arm curls, bench presses, and some of the calisthenics which can be performed using weights.

For instance, a pedometer or step counter can be worn on the user's belt to detect repeated movements which are performed during walking or running. A pedometer typically employs a mechanical or electrical sensor, such as a microelectromechanical system (MEMs) inertial sensor. Wrist worn devices are also available which use an accelerometer to count repetitive movements during weight training, such as sets and repetitions. For example, a set may include ten repetitions. An example is the POLAR F55®. Similarly, monitors which can be worn on top of a shoe, such as monitor 114 are available. An example is the POLAR 51 FOOTPOD®. In this product, an inertial sensor and DSP (digital signal processor) provide real time running speed, pace and distance. Such a product can be used during running or cycling, for instance. Monitors which are built in to a shoe or clothing are also available. Examples are provided by products under the brand of ADIDAS®-POLAR® PROJECT FUSION™. The techniques provided herein can be incorporated into products of these types, among others.

In the example provided, the user has a monitor 114 worn on his shoe 116 as well as the chest-worn monitor 102. The monitors 102 and 114 transmit wireless signals which indicate when a repetition of the monitory bodily activity has occurred. For example, the monitor 102 as a heart rate monitor can transmit a pulse or burst each time a heart beat is detected. In one approach, a pulse can include a signal modulated at a relatively low frequency of 5.3 kHz, or more generally, between 4.8 kHz and 5.8 kHz. Such low frequency signals are advantageous since they do not typically require approval by a government agency such as the FCC in the United States.

High frequency signals can also be used. An example is a 2.4 GHz signal. Such high frequency signals require a faster processor and thus may be more expensive and consume more power, and government approval may be required. Also, unlike low frequency signals, they are also susceptible to interference from electronic devices such as microwave ovens, cell phones, computers and wireless local area networks (WLAN) base stations used in computer networks.

The monitor 114 as a pace monitor can transmit a signal each time a step is detected. Similarly, the monitor 114 could detect a revolution of the user's feet, e.g., a chain ring revolution, on a stationary or moving bicycle as the user pedals while wearing the shoe 116.

A wireless signal transmitted from a monitor can be received at a receiver unit, where the signal is processed to provide an output in a visible and/or audible form for the user or other person. In some cases, the monitor transmits only and does not receive wireless signals or other signals while operating.

A console 120 is an example of a receiver unit. A console 120 can be mounted to exercise equipment such as a bicycle, treadmill, or stair climber machine, for instance, in a position in which it provides a display to the user 100. Or, the console 120 can be mounted or handheld, for use by another person such as an athletic trainer or medical personnel. In this example, the console has a display with a region 122 which provides a current heart rate, e.g., 120 beats per second (bps), a region 124 which indicates a elapsed exercise time, a region 126 which indicates a number of calories burned in the exercise session, and a region 128 which is a bar chart showing a history of the heart rate, e.g., over the past few minutes, relative to a target heart rate range which is between maximum (max) and minimum (min) levels. The console can also provide an audible output such as an alarm when the heart rate moves outside the target heart rate range, to signal to the user to move faster or slower.

Another example of a receiver unit is a wrist worn device 130 which provides an output in the form of a display of the current heart rate or other detected rate, for instance. An audible alarm or other output can also be provided as discussed. The receiver unit can be wrist worn, similar to a wrist watch, and may in fact have time keeping ability as well as the ability to provide an output based on the received wireless signal.

Another example of a receiver unit is a portable device 140 such as a cell phone, media player, personal digital assistance (PDA) or similar device. Such a device can be held in the user's hand or attached to the user's body, e.g., using a strap, or placed in a pocket of clothing worn by the user. The portable device 108 is held in an arm strap 106 as an example. The monitor 102 or 114 can communicate with the portable device 108 via a low frequency signal with the use of appropriate circuitry as described herein. The portable device 140 can provide a visual or audible output as discussed. In one approach, the user can receive an audible input from the portable device via an earphone such as an ear bud 112 which is connected by a wire 110 to the portable device 108. Such earphones are commonly used with portable media players. The audible output can include a synthesized voice which states the current heart rate at specified intervals, when the current heart rate is out of the target zone, or at other specified times.

Another example of a receiver unit is a wireless ear-worn device 150 which is similar to devices used to communicate with cell phones using Bluetooth (IEEE 802.15.1) transmissions. The monitor 102 or 114 can communicate with the ear-worn device 150 with the use of appropriate circuitry. Or, the monitor 102 or 114 can transmit a wireless signal to the portable device 140 such as a cell phone, where the portable device 140 in turn communicates with the wireless ear-worn device 150 to provide an audible output to the user 100, as discussed above. Many other variations are possible. Moreover, the wireless signal from a monitor can be received and processed by more than one receiver unit. In addition to real-time processing and updating of a heart rate or other parameter at a receiver unit, the receiver unit can record data from a monitor in a non-volatile memory such as a computer hard drive or flash memory for subsequent analysis.

Figure 2:
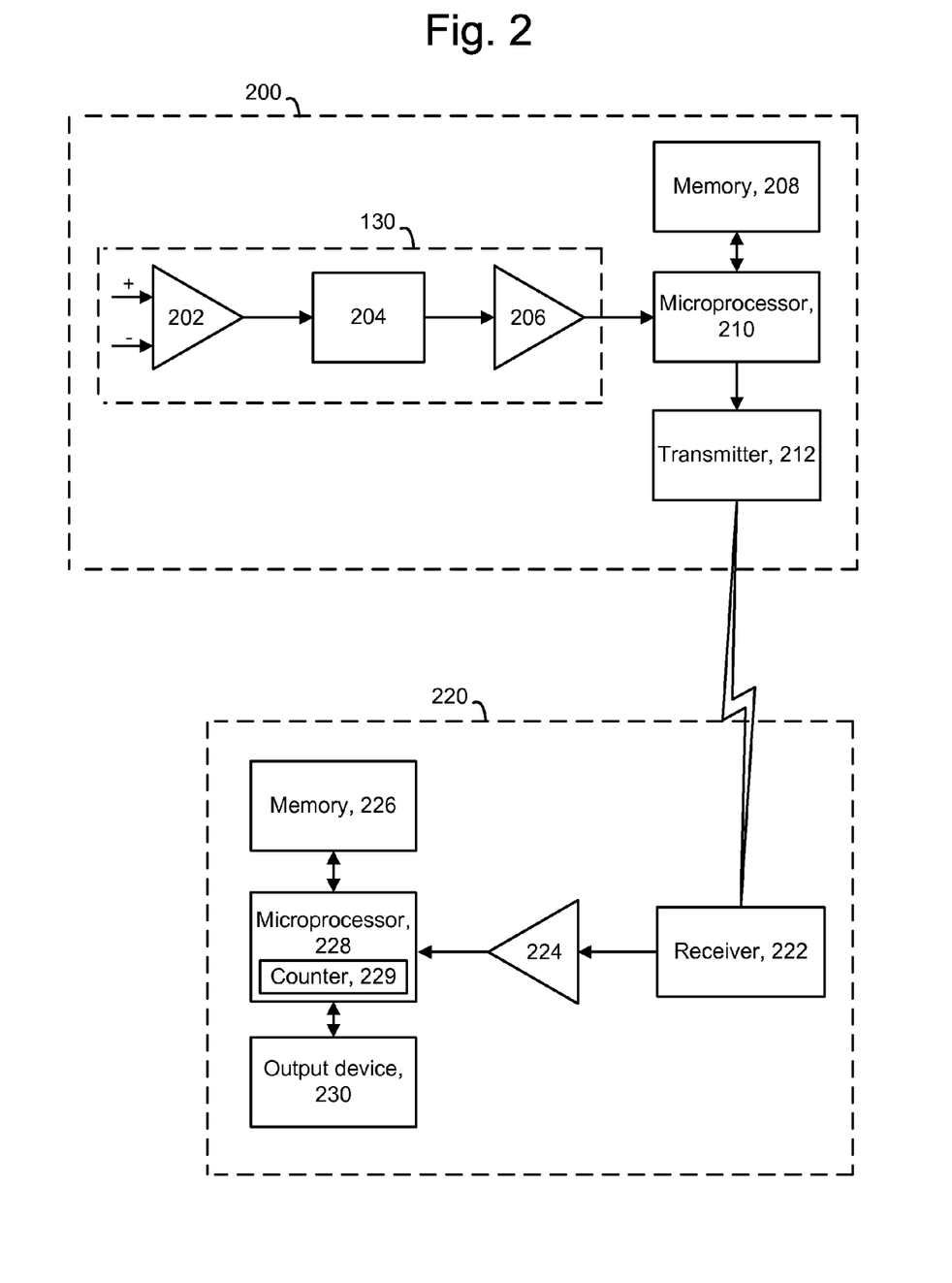
FIG. 2 depicts an example embodiment of a monitor and receiver unit.

FIG. 2 depicts an example embodiment of a monitor and receiver unit. A monitor 200 includes an amplifier circuit 130, which includes a differential amplifier or preamplifier 202, an amplifier/filter stage 204, and a final amplifier 206. In one implementation, the differential amplifier or preamplifier 202 receives an EKG signal of a user. The amplifier circuit 130 provides an amplified signal to a microprocessor 210. The microprocessor has a built-in A/D converter. The microprocessor samples and processes the amplified EKG signal to detect heart beats. Further details of such detection can be found, for instance, in U.S. Pat. No. 5,738,104 to Lo et al. and U.S. Pat. No. 5,876,350 to Lo et al., both of which are incorporated herein by reference. After a heart beat is detected, the microprocessor 210 will deliver a digital signal at each detected heart beat to a transmitter 212, which may include a transmitting coil and operate, e.g., by inductive or electromagnetic coupling. In one implementation, communication is one way from the microcontroller to the transmitter. The microprocessor 210 generates a digital burst signal, such as at 5.3 kHz, causing the coil in the transmitter to resonate and thereby transmit a wireless signal. The duration of the resonance and the corresponding pulse or burst which is transmitted is controlled by the microprocessor 210.

Thus, the transmitter can comprise an inductive resonator which provides each pulse in the wireless signal as an inductive burst, and the pulses generated by the monitor 200 each comprise an inductive burst, in one embodiment. The microprocessor 210 may access a memory 208 which includes code which is executable by the microprocessor 210. The memory 208 may include a tangible storage device such as a non-volatile memory, e.g., ROM, and a volatile memory, e.g., RAM, which store processor-readable code which is executed by one or more microprocessors to implement the functionality described herein.

As an option which reduces power consumption and cost, the output from the amplifier circuit 130 can be provided to a threshold detector. The threshold detector provides a digital output based on the level of the input. This digital output can be used to indicate the onset of a detected heart beat or other bodily action. In this case, no A/D conversion is needed. Microprocessor 210 can also run at a lower clock speed to save power.

The receiving unit 220 includes a receiver circuit 222, amplifier 224, microprocessor 228, memory 226 and output device 230. The microprocessor 228 may include a free running counter 229 which is used to select an identifier, as discussed below in connection with FIG. 6. The receiver circuit 220 may include coils which detect a magnetic field of the wireless signal and provide a corresponding signal to the amplifier circuit 224. In one approach, the amplifier circuit 224 includes a sensitive preamplifier followed by a signal amplifier. The amplified signal is processed by a microprocessor 228, which is responsive to code stored in a memory 226. The microprocessor can calculate a rate at which a bodily action of the user is performed based on a rate at which some or all of the pulses are received. The microprocessor provides a signal to an output device 230 to provide a visual and/or audible output as discussed.

Figure 3A:
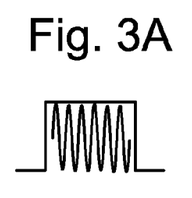
FIG. 3a depicts an example long burst which is transmitted by a monitor.
Figure 3B:
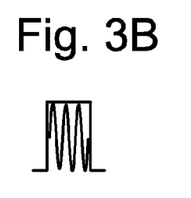
FIG. 3b depicts an example short burst which is transmitted by a monitor.

FIG. 3a depicts an example long burst which is transmitted by a monitor. FIG. 3b depicts an example short burst which is transmitted by a monitor. Each burst is interpreted as a single pulse as indicated by the pulse-shaped envelope.

In one embodiment, the duration of a burst is used as an identifier of the monitor, and different durations can be used to identify different monitors. With this type of positive identification, crosstalk and other types of interference can be handled. A long burst represents a pulse or burst whose duration is noticeably longer than a nominal, short burst. A short burst can be 5-10 milliseconds (msec.) for instance, while a longer burst can range from 20-250 msec., for instance. The long burst can be 2× or more longer than the short burst. The upper limit of the long burst depends on the application. For heart beat detection, a heart rate of 30-240 bpm may be covered. 240 bpm, or 4 beats per second, translates to a period between beats of 250 msec. The duration of the long burst should be less than the period between detected bodily events. In practice, a longer burst uses more power so the long burst need not be at the upper allowable limit. A long burst should have a duration which allows the burst to be distinguished from a short burst and from other long bursts. As an example, a long burst can be, e.g., at least 5-10 msec. longer than a short burst.

As a result, a predefined set of different durations which are identifiers for different user-worn monitors can be provided and stored in the monitor and receiver unit. Additionally, a binary code word can be assigned to each duration. For example, with $2^5=32$ code words, and a 5 msec. difference between long pulses, long pulse durations of 10, 15, 20, . . . , 155, 160, 165 msec. can be used in the predefined set. Corresponding example five-bit code words are 00000, 00001, 00010, . . . , 11101, 11110, 11111, respectively.

Figure 4A:
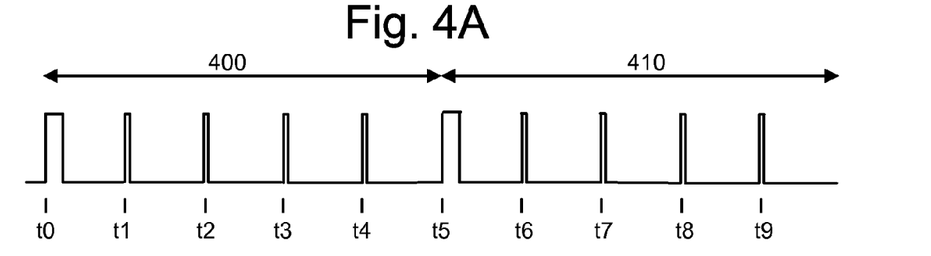
FIG. 4a depicts a time line of a wireless signal transmitted by a monitor, where a single long pulse is used in a cycle.

FIG. 4a depicts a time line of a wireless signal transmitted by a monitor, where a single long pulse is used in a cycle. The long pulse is an identifier pulse because its duration is used by the receiver unit as an identifier of the monitor. In one approach, a cycle includes a predefined number N of pulses. One or more long pulses can be provided in each cycle, or in every nth cycle, where n≧1. Moreover, the monitor and receiver unit can be preconfigured with knowledge of the number of pulses per cycle. Two example cycles 400 and 410 are depicted. Time increases moving to the right hand side of the figure. The pulse sizes and shapes are not necessarily to scale. In this example, one long pulse is provided per cycle, at t0 and t5. Additionally, the long pulse is at the start of a cycle, although this is not required. In each cycle, the long pulse is followed by other, shorter pulses of equal duration, e.g., 5-10 msec. Four short pulses are used as an example at t1-t4 and t6-t9.

Another option is to use all long pulses in each cycle. However, using a minimal number of long pulses mixed or interspersed among short pulses allows a monitor to be identified by a receiver unit while minimizing power consumption by the monitor. Generally, a long pulse can be transmitted every X beats, Y consecutive times to allow the receiver unit to synchronize to the correct monitor. X and Y can be integers which are greater than or equal to one. As an alternative, one or more long pulses can be transmitted in response to the first detected bodily action after every Z seconds, as discussed in connection with FIG. 4d.

In FIG. 4a, it can be seen that the wireless signal does not contain an identifier of the user-worn monitor other than an identifier which is provided by the duration of the identifier pulses, e.g., at t0 and t5. Also, the wireless signal does not contain pulses generated by the monitor at times other than when the bodily action of the user is detected. This is true because the transmitter does not provide the wireless signal with pulses at times other than when the bodily action of the user is detected. This is advantageous since the use of additional pulses, at times other than when the bodily action of the user is detected, consume power. Moreover, the shorter pulses each have a duration which does not identify the monitor and which is less than the duration of the long pulses, which identifies the monitor.

Figure 4B:
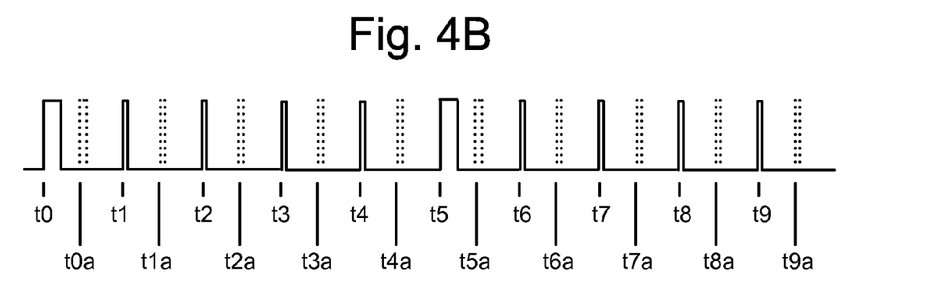
FIG. 4b depicts a time line of the wireless signal of FIG. 4a with the addition of crosstalk of short pulses.

FIG. 4b depicts a time line of the wireless signal of FIG. 4a with the addition of crosstalk of short pulses. Crosstalk can occur when two or more users who are wearing a common type of monitor are near one another, e.g., within a few feet. The receiver unit (subject receiver unit) which is intended to receive a wireless signal from a given monitor (subject monitor) also receives a wireless signal from one or more other monitors (crosstalk monitors) as undesired crosstalk. This can occur when users are exercising together, e.g., at stationary exercise equipment in a gym, or while jogging alongside one another in a group. A given receiver unit may experience different degrees of crosstalk at different times, as other users and their monitors move closer and away from the subject user and the subject monitor. In addition to crosstalk, other types of interference can be created by the user's environment, e.g., due to high voltage power lines, televisions, motor-driven exercise equipment, cell phones, and so forth. The subject receiver unit may be unable to process the wireless signal from the subject monitor, or provide an erroneous output, if the crosstalk cannot be handled. In this example, short crosstalk pulses from another monitor are indicated by dashed lines at t0a-t9a.

In some cases, a receiver unit can detect when crosstalk is present. For example, when the long pulse at t0 is received, the receiver unit can determine an expected time to receive a next pulse, particularly if information from previous pulses has been used to determine a current rate of detection of the bodily action. Typically, the time interval between successive pulses will be relatively uniform, so that an expected time interval at which a next pulse is received can be estimated with good accuracy based on the time interval at which the last pulse was received. Thus, knowing that a next pulse should be received at or near t1, the presence of the crosstalk pulse at t0a can be identified as crosstalk, and ignored, by a receiver unit. Another example technique to detect crosstalk involves detecting the amplitude of each pulse, where higher amplitude pulses are assumed to be from the subject monitor, based on the assumption that the subject monitor is closer to the subject receiver unit than the crosstalk monitor. See US patent application publication no. US2009/0043217 to Hui et al., published Feb. 12, 2009, and incorporated herein by reference, for further details.

In some cases, the crosstalk pulses may be sufficiently close to the pulses of the subject monitor so that the receiver unit cannot distinguish the correct pulses. In such cases, the microprocessor of the receiver unit can enter a special crosstalk mode in which it only synchronizes with the long pulses, but not the short pulses, to determine the rate of the bodily action. The rate can be determined knowing the time interval between the long pulses and the number of short pulses between the long pulses. For example, a rate based on the long pulses at t5 and t0, with four pulses between them, is 5 beats/(t5—t0). In this case, the rate is updated less often than every pulse. The microprocessor can continue to detect the short pulses, whether they are crosstalk or not, to determine when crosstalk is no longer present at a threshold level, and to return to another, baseline mode in which case the microcontroller of the receiver unit synchronizes with each pulse to update the rate.

A threshold level of crosstalk can be defined which the microcontroller uses to determine whether to change its operating mode. The threshold level may be met, e.g., if one or more crosstalk pulses are detected in one or more cycles, even if it is determined that they have highly inconsistent timing and therefore can be ignored. Or, the threshold level may be met if a specified number of crosstalk pulses are detected in a cycle, and this is repeated for a specified number of cycles. Or, the threshold level may be met if one or more crosstalk pulses are detected which render it impossible to accurately detect the short pulses in one or more cycles. Or, the threshold level may be met if one or more crosstalk pulses are detected which have a specified amplitude, such as an amplitude which is a specified portion of the non-crosstalk pulses. Or, the threshold level may be met if one or more crosstalk pulses are detected which have a discernible amplitude. Other definitions of the threshold level may be used as well.

The microprocessor can change back and forth between the crosstalk mode and the baseline mode as the level of crosstalk changes over time. In this way, the highest possible update rate is maintained whenever possible.

In this example, the monitor of the subject user provides a long pulse as an identifier in each cycle, while the crosstalk is provided by a crosstalk monitor which does not use a long pulse. Another example scenario, discussed next, involves both monitors using long pulses.

Figure 4C:
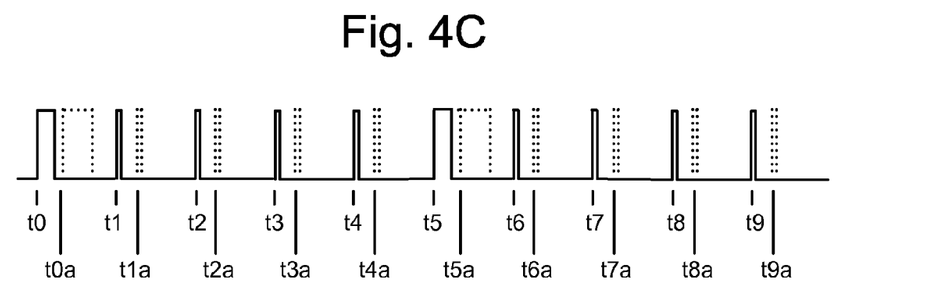
FIG. 4c depicts a time line of the wireless signal of FIG. 4a with the addition of crosstalk of long and short pulses.

FIG. 4c depicts a time line of the wireless signal of FIG. 4a with the addition of crosstalk of long and short pulses. As before, the pulses from the given monitor are at t0-t9 and the pulses from the other monitor are indicated by dashed lines at t0a-t9a. As before, the presence of the crosstalk pulses can be identified as crosstalk by a subject receiver unit when they are received at an inconsistent time. In one approach, the rise of each pulse is interpreted as the received time of the pulse, so that long and short pulses are interpreted consistently, and a long pulse is not interpreted as having arrived later than it did. Also, by interpreting the rise of each pulse as the received time of the pulse, compatibility is provided with a receiver unit which does not distinguish a long pulse from a short pulse, or is otherwise blind to pulse width.

A further mechanism for detecting crosstalk is to compare the duration of each long pulse to the known duration which has been associated with the subject monitor. If the duration is inconsistent with the known duration, either shorter or longer by a specified margin such as 1-2 msec., the long pulse can be determined to be crosstalk. Moreover, a determination that crosstalk is present can be based on analysis of the duration and/or timing of more than one pulse. In this case, a pulse that appears to be crosstalk may not trigger the crosstalk mode in the microprocessor of the subject receiver unit until the determination is confirmed by one or more other pulses in the same cycle and/or one or more other cycles. A pulse that appears to be crosstalk can be ignored or skipped at the subject receiver unit for purposes of determining a rate of received pulses. The timing of the next pulse which does not appear to be crosstalk, with knowledge of the number of skipped pulses, can be used to determine the next updated of the rate, in one approach.

In some cases, a crosstalk pulse may overlap with a pulse from the subject monitor such that a pulse from the subject monitor is corrupted and appears to be longer than it is. In such cases, the enlarged pulse may be ignored by the subject receiver unit, and the next uncorrupted pulse used to determine the rate. Generally, crosstalk reduction is a probabilistic technique which attempts to account for the most probable scenarios.

Figure 4D:
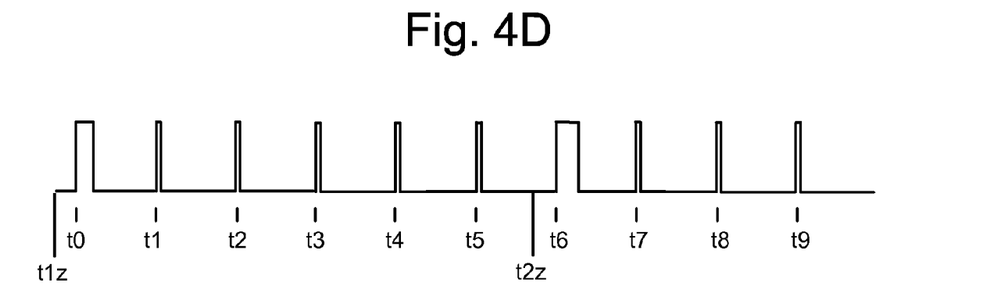
FIG. 4d depicts a time line of a wireless signal transmitted by a monitor, where a single long pulse is used after every Z seconds.

FIG. 4d depicts a time line of a wireless signal transmitted by a monitor, where a single long pulse is used after every Z seconds. Instead of transmitting a long pulse based on a pulse position within a cycle or based on a pulse count, one or more long pulses can be transmitted based on specific time intervals. Fixed or varying intervals can be used. In an approach which uses a fixed interval, a long pulse is transmitted based on a specified period such as every Z seconds. For example, assume a period begins at $tz1$, just before the long pulse at $t0$, and Z seconds later occurs just before $t6$, at $t2z$. The period is $t2z-t1z$. In this case, the next pulse after $t2z$ which is transmitted will be a long pulse, at $t6$. In this approach, the number of short pulses between long pulses can vary as the rate of the detected bodily action varies. In one approach, the heart rate is based on the temporal spacing of each pulse, including both the long and short pulses.

Figure 5A:
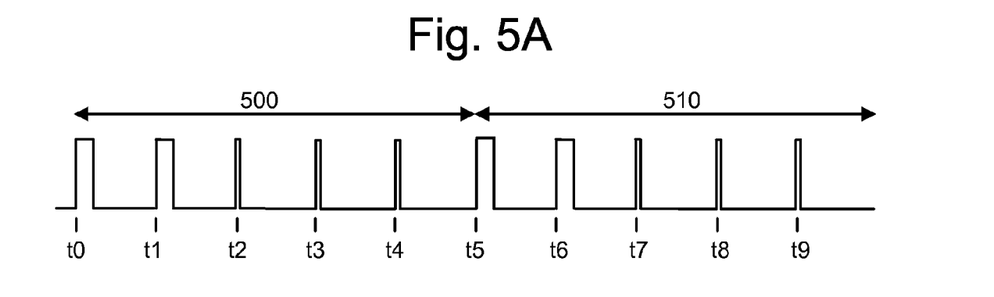
FIG. 5a depicts a time line of a wireless signal transmitted by a monitor, where two long pulses are used in a cycle.

FIG. 5a depicts a time line of a wireless signal transmitted by a monitor, where two long pulses are used in a cycle. By having multiple long pulses in a cycle, timing information can be gained faster by the receiver unit even when the presence of crosstalk renders undistinguishable the other, short pulses which are meant for the receiver unit. Thus, the receiver unit can synchronize sooner with the monitor. For example, long pulses are provided at $t0$ and $t1$ in a cycle 500, and at $t5$ and $t6$ in a cycle 510. Short pulses are provided at $t2-t4$ and $t7-t9$. The long pulses can be consecutive but this is not necessary as long as their relative positions (e.g., the number of short pulses between them, which is zero or more) is known. Here, once the long pulses at $t0$ and $t1$ are received, the interval between them indicates a rate, as well as the expected interval of the next pulse, which is a short pulse in this example. Thus, the rate can be determined right away, and the presence of a pulse which is inconsistent with the expected timing can be identified as crosstalk.

Figure 5B:
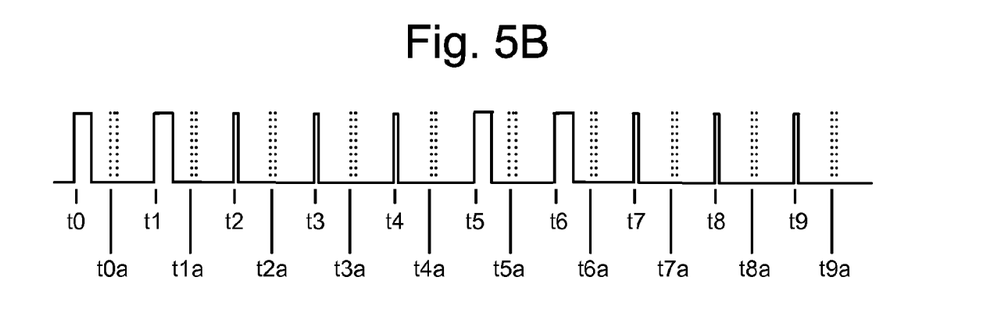
FIG. 5b depicts a time line of the wireless signal of FIG. 5a with the addition of crosstalk of short pulses.

FIG. 5b depicts a time line of the wireless signal of FIG. 5a with the addition of crosstalk of short pulses at $t0a-t9a$. Here, the crosstalk pulses can likely be identified and distinguished from the correct pulses, as discussed previously. If the crosstalk pulses cannot be distinguished, the microprocessor of the receiver unit can enter the crosstalk mode. In this case, the timing of the long pulses, combined with knowledge of the number of short pulses between the long pulses, can be used to update the rate when each long pulse is received.

Figure 5C:
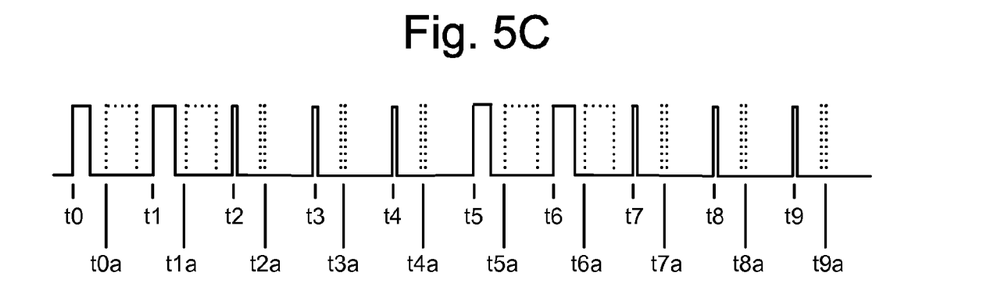
FIG. 5c depicts a time line of the wireless signal of FIG. 5a with the addition of crosstalk of long and short pulses.

FIG. 5c depicts a time line of the wireless signal of FIG. 5a with the addition of crosstalk of long and short pulses. In this example, the subject monitor and the crosstalk monitor both use two long pulses (e.g., of different durations) as identifiers in each cycle. As before, the pulses from the subject monitor are at $t0-t9$ and the pulses from the crosstalk monitor are indicated by dashed lines at $t0a-t9a$. As discussed before in connection with FIG. 4c, the timing of the pulses, as well as the duration of the long pulses, can be used to detect whether or not a threshold level of crosstalk is present.

Variations and combinations of the approaches in FIGS. 4a, 4d and 5a can also be used. For example, a transmission may switch between the approaches at different times. For instance, one or more cycles can be used which each have one long pulse, followed by one or more cycles which each have two or more consecutive pulses. Thus, the long pulses can appear consecutively and/or non-consecutively in a wireless signal.

Figure 6:
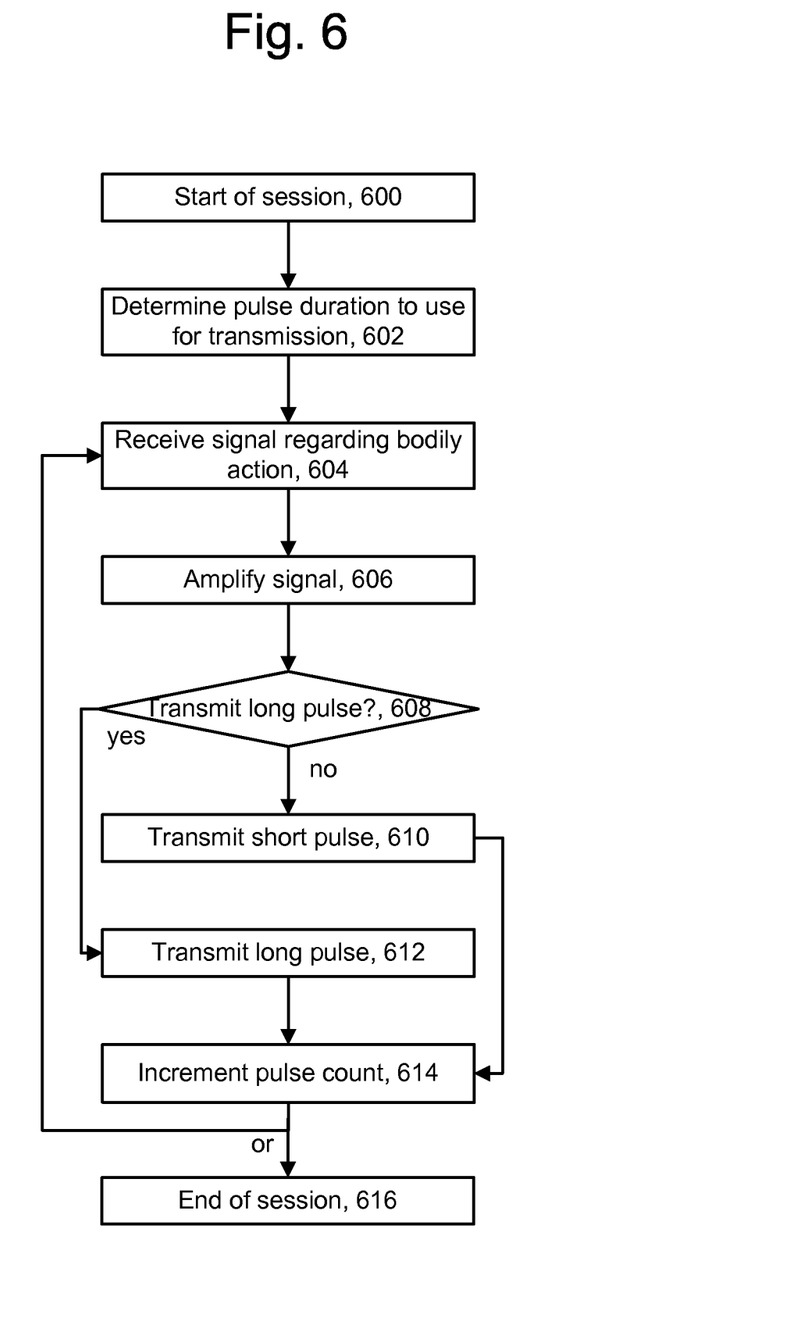
FIG. 6 depicts an example method performed by the monitor of FIG. 1.

FIG. 6 depicts an example method performed by the monitor of FIG. 1. A session such as an exercise session starts at step 600. This may occur when the user attaches the monitor to his or her body. For example, a chest-worn monitor may start transmitting when it is placed in contact with the user's skin and thereby picks up the EKG signal of the user. In some scenarios, no crosstalk is present when the session begins. For instance, a first user may be jogging along with a chest-mounted monitor and a wrist-mounted receiver unit. In this case, there is no problem with crosstalk and the receiver unit can quickly synchronize with the monitor. The first user then meets with a friend who also has a receiver unit synchronized to his monitor, and continues jogging with the friend. In this case, the friend's monitor may cause crosstalk to the receiver unit of the first user. However, this can be accommodated using the techniques provided herein. Moreover, the level of the crosstalk may fall below or rise above a threshold level as the users move further or closer apart, respectively.

Step 602 includes determining a pulse duration to use for transmission. A monitor may be hard-coded with a specific long pulse duration to use, or it may selected the duration from a predefined set of different durations which are identifiers for different user-worn monitors. For example, the predefined set can be stored in the memory 226 of the receiver unit (FIG. 2). The microcontroller can set the duration non-deterministically by accessing the memory to select one of the durations from the predefined set of different durations.

In one approach, the microprocessor uses a free running counter 229, which is a counter than is constantly up from zero, for instance, until a maximum value is reached, at which time the counter restarts the counting. Such a counter can be implemented in hardware, for instance, and provide a value which is mapped to one of the available durations. The value of the count can be stored and accessed from a memory register. A non-deterministic selection of a duration includes a random or pseudo-random selection. Other possible techniques for selecting a duration use a random number generator which is realized by hardware and/or software. A random number generator can be implemented by a software algorithm that runs continuously with an output number that changes randomly. Another approach is to determine the long pulse duration by counting random events such as a start or end of a session. Another approach is to determine the long pulse duration based on a rate acquisition time or the rate itself. For example, when a user ends an exercise session and removes the monitor, the monitor can record and store the current rate based on the timing between the last two consecutive transmitted pulses. This stored value can be accessed when a new session is later started and used as a seed input to a random number generator, for instance, to determine a value which is mapped to one of the predefined available pulse durations.

As discussed, various transmission patterns can be used. Generally, the transmission includes long pulses interspersed among other, short pulses. The long pulses can appear consecutively and/or non-consecutively. A transmission pattern can be used based on repeated cycles, where each cycle has the same pattern, and one or more long pulses are in predefined positions within a cycle, interspersed among the short pulses. The one or more long pulses in a cycle can be at the start of a cycle or other relative position within a cycle, in a cycle-based pattern. Or, a time-based pattern can be used, e.g., as discussed in connection with FIG. 4d, where long pulses are transmitted at specified time intervals, such as periodically, interspersed among the short pulses. When a time for transmitting a long pulse is reached, the long pulse is transmitted when the next bodily action is detected.

At step 604, the monitor receives a signal regarding a bodily action, such as an EKG signal indicating that a heart beat has occurred, or a signal from a pedometer which indicates that the user has taken a step or performed an instance, e.g., occurrence, of a repetitive physical movement during exercise. For example, the repetitive movement may be jogging, where an instance of the movement is each step. Where the repetitive bodily action is the heart beating, an instance of the bodily action is one heart beat. At step 606, the monitor amplifies the signal. At decision step 608, if a condition is met for transmitting a long pulse, the monitor transmits a long pulse, at step 612. The condition can be based on a cycle-based pattern or a time-based pattern, for instance, as discussed.

At decision step 608, if the condition for transmitting a long pulse is not met, the monitor transmits a short pulse, at step 610. At step 614, a pulse counter is incremented. The pulse counter can be used to track the current position within a cycle and to determine when to start a new cycle. The monitor waits to receive the next signal regarding the bodily action, at step 604, or the session ends at step 616.

A session can end when the user takes the monitor off, or manually turns the monitor off, for instance. A timeout period such as several seconds may be enforced by the monitor and/or receiver unit before the session of exercise is determined to end, at which time the identification of the monitor may be discarded. In a subsequent new session, the monitor can select another pulse duration as its identifier, and the receiver unit again identifies the monitor based on the newly-chosen duration of the identifier pulses. For example, a session can be defined as a time period in which a user wears a chest strap, where the end of the session occurs when the user removes the chest strap. The microcontroller of the monitor can be configured so that the intermittent disconnection of the chest strap does not create a new session. For example, if the removes the chest strap but reattaches it within next "x" seconds (e.g., 15, 30 or 60 seconds), the session is maintained, but if there is a gap of more than "x" seconds, a new session is started and assigned a new long pulse width.

In this case, the pulse duration and therefore the monitor identifier is dynamic. Or, the pulse duration may be hard-coded into a matched set of a monitor and a receiver unit, and different respective pulse durations may be hard-coded into different respective matched monitor-receiver unit sets.

The communication may be one-way from the monitor to the receiver unit so that the long pulse duration is not changed once a session begins.

Figure 7:
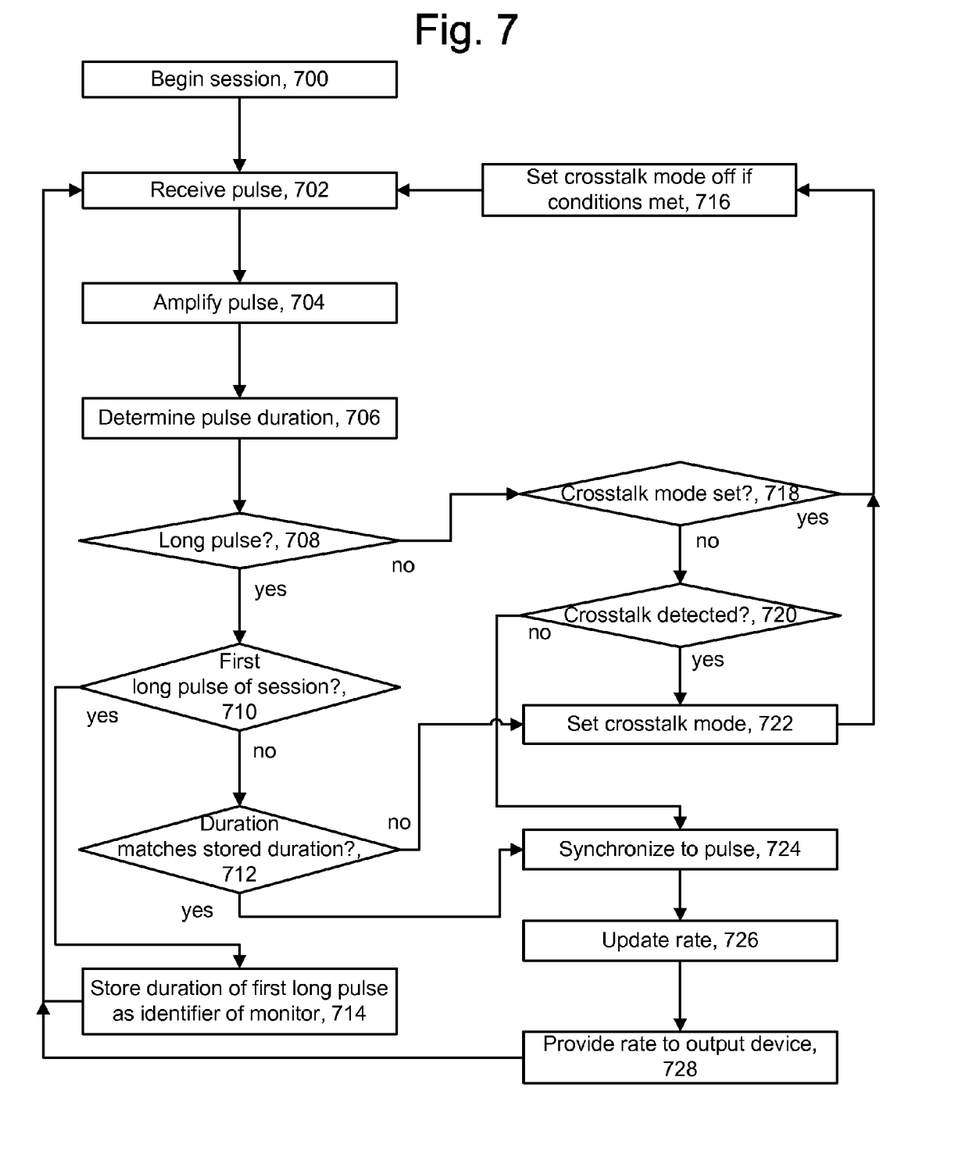
FIG. 7 depicts an example method performed by the receiver unit of FIG. 1.

FIG. 7 depicts an example method performed by the receiver unit of FIG. 1. The receiver unit begins a session at 700, such as when it is powered on. As an example, a receiver unit which is mounted to exercise equipment may begin a session and exit a sleep mode when the user starts to move on the exercise equipment, such as walking on a treadmill. At step 702, a pulse is received from the monitor. Each pulse represents a respective instance of the bodily action which is monitored. As mentioned, the bodily action can be a heartbeat. Or, each respective instance of the bodily action can be a respective instance of a repetitive physical movement performed by the user during exercise.

At step 704, the pulse is amplified. At step 706, the pulse duration is determined, e.g., as the time interval between the leading and trailing edges of the pulse. At decision step 708, if the pulse is a long pulse, decision step 710 determines if it is the first long pulse of the session. If it is the first long pulse of the session, its duration is stored as an identifier of the monitor at step 714. Data which represents the duration itself as a time value can be stored, or the duration can be mapped to a code word which is stored. An additional check can be made to ensure that the duration is consistent with a pre-defined set of durations which are available identifiers of different monitors. For example, the duration may be required to match, within a tolerance, one of the available durations.

At decision step 710, if the long pulse is not the first long pulse of the session, a decision step 712 determines if the duration matches a previously-stored duration within a tolerance of, e.g., +/−1-2 msec. If there is a match, the microcontroller synchronizes to the pulse at step 724. That is, the microcontroller uses the timing of the pulse. At step 726, the rate of the bodily action is updated based on the pulse, and at step 728, the newly-updated rate is provided to an output device. A next pulse is then received at step 702.

If decision step 712 determines that the pulse duration does not match the stored duration, a crosstalk mode can be set for the microprocessor at step 722, in one possible approach. As mentioned previously, various criteria can be used to determine whether a threshold level of crosstalk is detected and to decide whether or not to set a crosstalk mode to accommodate the crosstalk. The mode can switch from the crosstalk mode back to the baseline mode if certain conditions are met, at step 716, such as the crosstalk level falling below a threshold level. Switching between modes may be controlled so that it does not occur too frequently. For example, mode switching may occur only after a time interval has passed or a minimum number of pulses have been detected. A next pulse is then received at step 702.

If decision step 708 determines that the current pulse is not a long pulse, decision step 718 determines if the crosstalk mode has been previously set. If the crosstalk mode is set, steps 716 and 702 follow. In this case, the microprocessor does not synchronize to the short pulse so that its timing information is not used to update the rate. If the crosstalk mode is not set at decision step 718, decision step 720 determines if a threshold level of crosstalk is currently detected. If the threshold level of crosstalk is detected, the crosstalk mode is set at step 722. If decision step 720 determines that the threshold level of crosstalk is not detected, steps 724, 726 and 728 are performed as discussed.

Generally, when the receiver unit is powered on and the monitor is transmitting, a time period of a few seconds may pass before the receiver unit synchronizes to the monitor and outputs a rate. During this time period, or after, the receiver unit sees a long duration pulse and uses it as an identifier of the monitor, and continues its synchronization with that monitor.

The foregoing detailed description of the technology herein has been presented for purposes of illustration and description. It is not intended to be exhaustive or to limit the technology to the precise form disclosed. Many modifications and variations are possible in light of the above teaching. The described embodiments were chosen to best explain the principles of the technology and its practical application to thereby enable others skilled in the art to best utilize the technology in various embodiments and with various modifications as are suited to the particular use contemplated. It is intended that the scope of the technology be defined by the claims appended hereto.

We claim:

1. A receiver unit, comprising:
   a receiver circuit, the receiver circuit receives a wireless signal from a user-worn monitor, the wireless signal includes respective pulses generated by the user-worn monitor, each respective pulse is generated when a respective instance of a bodily action of the user is detected, and the respective pulses include identifier pulses which each have a duration which identifies the user-worn monitor, interspersed among other pulses, where the respective pulses are provided in successive cycles including at least first and second cycles;

an amplifier circuit associated with the receiver circuit, the amplifier circuit provides an amplified signal based on the wireless signal;

a microprocessor associated with the amplifier circuit, the microprocessor operates in a crosstalk mode in which it processes the amplified signal to interpret the duration of each of the identifier pulses as an identifier of the user-worn monitor, synchronizes with the identifier pulses, and determines a rate of the bodily action based on: (a) a time interval between at least one identifier pulse in the first cycle and at least one identifier pulse in the second cycle, and (b) a number of pulses, including at least one of the other pulses, between the at least one identifier pulse in the first cycle and the at least one identifier pulse in the second cycle; and an output device associated with the microprocessor, the output device provides an output based on the rate of the bodily action.

2. The receiver unit of claim 1, wherein:
the microprocessor operates in the crosstalk mode when it detects a threshold level of crosstalk in the amplified signal and in a baseline mode when it does not detect the threshold level of crosstalk in the amplified signal, wherein, in the baseline mode, the microprocessor processes the amplified signal to synchronize with the identifier pulses and with the other pulses, and determines the rate of the bodily action based on timing of the identifier pulses and the other pulses.

3. The receiver unit of claim 2, wherein:
the microprocessor does not detect the threshold level of crosstalk in the amplified signal when it does not detect pulses which are inconsistent with a previously determined rate of the bodily action, and the microprocessor does detect the threshold level of crosstalk in the amplified signal when it does detect pulses which are inconsistent with the previously determined rate of the bodily action.

4. The receiver unit of claim 1, wherein:
the microprocessor interprets the duration of each of the identifier pulses as the identifier of the user-worn monitor based on the duration of each of the identifier pulses being consistent with a predefined set of different durations which are available identifiers for different user-worn monitors.

5. The receiver unit of claim 1, wherein:
the wireless signal does not contain an identifier of the user-worn monitor other than an identifier which is provided by the duration of the identifier pulses.

6. The receiver unit of claim 1, wherein:
the wireless signal does not contain pulses generated by the user-worn monitor at times other than when the bodily action of the user is detected.

7. The receiver unit of claim 1, wherein:
the pulses generated by the user-worn monitor each comprise an inductive burst; and
the receiver circuit comprises an inductive resonator.

8. The receiver unit of claim 1, wherein:
the other pulses each have a duration which does not identify the user-worn monitor and which is less than the duration which identifies the user-worn monitor.

9. The receiver unit of claim 1, wherein:
each respective instance of the bodily action is a heartbeat.

10. The receiver unit of claim 1, wherein:
each respective instance of the bodily action is a respective instance of a repetitive physical movement performed by the user during exercise.

11. A receiver unit, comprising:
a receiver circuit, the receiver circuit receives a wireless signal from a user-worn monitor, the wireless signal includes respective pulses generated by the user-worn monitor, each respective pulse is generated when a respective instance of a bodily action of the user is detected, and the respective pulses include: (a) at least two consecutive identifier pulses which each have a duration which identifies the user-worn monitor, and (b) other pulses;

an amplifier circuit associated with the receiver circuit, the amplifier circuit provides an amplified signal based on the wireless signal;

a microprocessor associated with the amplifier circuit, the microprocessor processes the amplified signal to interpret the duration of each of the at least two consecutive identifier pulses as an identifier of the user-worn monitor, determines a time interval between each of the at least two consecutive identifier pulses, synchronizes with the other pulses based on the time interval, and determines a rate of the bodily action based on timing of the other pulses; and an output device associated with the microprocessor, the output device provides an output based on the rate of the bodily action.

12. The receiver unit of claim 11, wherein:
the microprocessor determines the rate of the bodily action based also on the time interval between each of the at least two consecutive identifier pulses.

13. The receiver unit of claim 11, wherein:
the microprocessor interprets the duration of each of the at least two consecutive identifier pulses as the identifier of the user-worn monitor based on the duration of each of the at least two consecutive identifier pulses being consistent with a predefined set of different durations which are available identifiers for different user-worn monitors.

14. The receiver unit of claim 11, wherein:
the wireless signal does not contain pulses generated by the user-worn monitor at times other than when the bodily action of the user is detected.

15. The receiver unit of claim 11, wherein:
the other pulses each have a duration which does not identify the user-worn monitor and which is less than the duration which identifies the user-worn monitor.

16. A user-worn monitor, comprising:
an amplifier circuit, the amplifier circuit receives a signal regarding a bodily action of a user and provides a corresponding amplified signal;
a microcontroller associated with the amplifier circuit; and
a transmitter associated with the microcontroller and the amplifier circuit, the transmitter provides a wireless signal based on the amplified signal, the wireless signal includes respective pulses, where each respective pulse is generated when a respective instance of the bodily action is detected, and the respective pulses include identifier pulses which each have a duration which is set in response to the microcontroller to identify the user-worn monitor, interspersed among other pulses.

17. The user-worn monitor of claim 16, wherein:
the identifier pulses include groups of at least two consecutive identifier pulses interspersed among the other pulses.

18. The user-worn monitor of claim 16, wherein:
the received signal is an electrocardiogram signal; and
each respective instance of the bodily action is a heartbeat.

19. The user-worn monitor of claim 16, wherein:
the wireless signal does not contain an identifier of the user-worn monitor other than an identifier which is provided by the duration of each of the identifier pulses.

20. The user-worn monitor of claim 16, wherein:
the other pulses each have a duration which does not identify the user-worn monitor and which is less than the duration of each of the identifier pulses.

21. The user-worn monitor of claim 16, wherein:
the transmitter does not provide the wireless signal with pulses at times other than when the bodily action of the user is detected.

22. The user-worn monitor of claim 16, wherein:
the transmitter comprises an inductive resonator which provides each pulse in the wireless signal as an inductive burst.

23. The user-worn monitor of claim 16, wherein:
the microcontroller sets the duration non-deterministically.

24. The user-worn monitor of claim 16, further comprising:
a free-running counter which is used by the microcontroller to set the duration non-deterministically.

25. The user-worn monitor of claim 16, further comprising:
a memory which stores a predefined set of different durations which are available identifiers for different user-worn monitors, the microcontroller sets the duration non-deterministically by accessing the memory to select one of the durations from the predefined set of different durations.

26. The user-worn monitor of claim 16, wherein:
each respective instance of the bodily action is a respective instance of a repetitive physical movement performed by the user during exercise.

27. A method for use at a receiver unit, comprising:
receiving a wireless signal from a user-worn monitor, the wireless signal includes respective pulses generated by the user-worn monitor, each respective pulse is generated when a respective instance of a bodily action of the user is detected, and the respective pulses include a first cycle of pulses which include at least one identifier pulse and other pulses, which are not identifier pulses, and a second cycle of pulses which include at least one identifier pulse and other pulses, which are not identifier pulses, the at least one identifier pulse of the first cycle and the at least one identifier pulse of the second cycle each have a duration which identifies the user-worn monitor;
providing an amplified signal based on the wireless signal;
processing the amplified signal to: (i) interpret the durations of the at least one identifier pulse of the first cycle and of the at least one identifier pulse of the second cycle as identifiers of the user-worn monitor, based on the durations being consistent with a predefined set of different durations which are available identifiers for different user-worn monitors, and (ii) to determine a rate of the bodily action; and
provide, on an output device, an output which is based on the rate of the bodily action.

28. The method of claim 27, wherein:
each respective instance of the rate of the bodily action is determined based on timing of the at least one identifier pulse of the first cycle and the at least one identifier pulse of the second cycle.

29. The method of claim 27, wherein:
the rate of the bodily action is determined based on a number of pulses, including the other pulses, in each of the first and second cycles.

30. A method for use at a user-worn monitor, comprising:
detecting a start of an exercise session of a user and, in response, selecting a pulse duration as an identifier for the user-worn monitor from a predefined set of different pulse durations which are available identifiers for different user-worn monitors;
during the exercise session, receiving a signal regarding a bodily action of a user and providing a corresponding amplified signal; and
transmitting a wireless signal based on the amplified signal, the wireless signal includes respective pulses, where each respective pulse is generated when a respective instance of the bodily action is detected, and the respective pulses include identifier pulses which each have the selected pulse duration, and other, shorter-duration pulses.

31. The method of claim 30, wherein:
the respective pulses are transmitted in successive cycles, where each cycle includes at least one identifier pulse and a plurality of the other, shorter pulses.

* * * * *